United States Patent
Kaiser et al.

(10) Patent No.: US 7,767,988 B2
(45) Date of Patent: Aug. 3, 2010

(54) PARTICLE THERAPY SYSTEM

(75) Inventors: Werner Kaiser, Erlangen (DE); Eberhard Sust, Hofheim am Taunus (DE)

(73) Assignees: Siemens Aktiengesellschaft (DE); MT Mechatronics GmbH (DE)

( * ) Notice: Subject to any disclaimer, the term of this patent is extended or adjusted under 35 U.S.C. 154(b) by 153 days.

(21) Appl. No.: 12/201,782

(22) Filed: Aug. 29, 2008

(65) Prior Publication Data

US 2009/0065717 A1    Mar. 12, 2009

(30) Foreign Application Priority Data

Sep. 6, 2007    (DE) .................... 10 2007 042 340

(51) Int. Cl.
*A61N 5/10*    (2006.01)
*A61N 5/00*    (2006.01)

(52) U.S. Cl. ................... 250/492.3; 250/505.1; 378/62; 378/64; 378/65; 378/209

(58) Field of Classification Search .............. 250/505.1, 250/492.1, 492.21, 492.3; 378/197, 62–65, 378/196–198, 208, 209

See application file for complete search history.

(56) References Cited

U.S. PATENT DOCUMENTS

| | | | |
|---|---|---|---|
| 3,466,439 A | | 9/1969 | Setala |
| 5,321,271 A | | 6/1994 | Schonberg et al. |
| 6,508,586 B2 * | 1/2003 | Oota | ........................ 378/196 |
| 6,520,677 B2 * | 2/2003 | Iizuka | ........................ 378/209 |
| 6,842,502 B2 * | 1/2005 | Jaffray et al. | .................. 378/65 |
| 6,888,919 B2 * | 5/2005 | Graf | ............................ 378/65 |
| 7,173,265 B2 * | 2/2007 | Miller et al. | .............. 250/492.3 |
| 7,193,227 B2 | 3/2007 | Hiramoto et al. | |
| 7,200,202 B2 * | 4/2007 | Kusch et al. | .................. 378/65 |
| 7,280,633 B2 * | 10/2007 | Cheng et al. | .................. 378/65 |
| 7,446,328 B2 * | 11/2008 | Rigney et al. | ............. 250/492.3 |
| 2001/0007588 A1 * | 7/2001 | Iizuka | ........................ 378/209 |
| 2002/0039403 A1 * | 4/2002 | Oota | ........................ 378/196 |
| 2003/0007601 A1 * | 1/2003 | Jaffray et al. | .................. 378/65 |
| 2004/0024300 A1 * | 2/2004 | Graf | ........................... 600/407 |
| 2005/0281387 A1 * | 12/2005 | Kusch et al. | ................. 378/197 |
| 2005/0281389 A1 | 12/2005 | Kusch et al. | |

(Continued)

FOREIGN PATENT DOCUMENTS

DE    42 14 087    5/1993

(Continued)

OTHER PUBLICATIONS

Partikeltherapie (Aug. 14, 2009); http://de.wikipedia.org/wiki/Partikel-Therapie; Others; 2009.

(Continued)

*Primary Examiner*—Bernard E Souw
(74) *Attorney, Agent, or Firm*—Brinks Hofer Gilson & Lione

(57) ABSTRACT

A particle therapy system is provided. The particle therapy system includes an imaging unit and a rotatable gantry with an irradiation unit. The irradiation unit projects into an irradiation room delimited by a wall. The imaging unit is arranged on a C-arm. The C-arm is operable to be moved between a retracted parking position and an extended diagnostic position for imaging purposes.

15 Claims, 2 Drawing Sheets

U.S. PATENT DOCUMENTS

2006/0002511 A1* 1/2006 Miller et al. .................. 378/65
2008/0219407 A1* 9/2008 Kaiser et al. .................. 378/65

FOREIGN PATENT DOCUMENTS

| DE | 199 07 771 | 8/2000 |
| DE | 199 58 864 | 6/2001 |
| DE | 100 47 364 A1 | 4/2002 |
| DE | 10 2004 062 473 A1 | 4/2006 |
| DE | 10 2005 041 122 | 5/2007 |
| DE | 10 2005 059 210 | 6/2007 |
| EP | 1 479 411 | 11/2004 |
| EP | 1 709 994 A1 | 10/2006 |

OTHER PUBLICATIONS

Thomas F. Delaney et al., "Proton and Charged Particle Radiotherapy", 2008 by Lippincott Williams & Wilkins (Wolters Kluwer), p. 97:Others; 2008.

HIT, Heidelberg Ion-Beam Therapy Centre, Mar. 2007, Universitätsklinikum, Broschüre; Others; 2007.

German opposition dated Aug. 19, 2009 for DE 10 2007 042 340.5-54 with English translation.

German Office Action dated Jun. 11, 2008 with English translation.

Kamada et al., "A Horizontal CT System Dedicated to Heavy-Ion Beam Treatment," Radiotherapy and Oncology 50 (1999), pp. 235-237.

* cited by examiner

PARTICLE THERAPY SYSTEM

The present patent document claims the benefit of the filing date of DE 10 2007 042 340.5, filed Sep. 6, 2007, which is hereby incorporated by reference.

BACKGROUND

The present embodiments relate to a particle therapy system including a rotatable gantry with an irradiation unit, which projects into an irradiation room delimited by a wall.

Particle therapy may be used to treat cancers. During particle therapy, a particle beam, for example, composed of protons or ions, is generated in an accelerator. The particle beam is guided in an irradiation channel and enters an irradiation room via an outlet aperture of an irradiation unit.

The gantry includes an approximately cylindrical irradiation room into which a patient couch is introduced. For precise treatment, the tissue of the patient to be irradiated (e.g., the tumor) is positioned as exactly as possible in the isocenter of the system. An imaging system is used to verify the position of the tumor. The imaging system encompasses the patient to the greatest possible extent while he lies on the patient couch in the irradiation room. For position verification, X-ray images are recorded from various angles. The imaging unit includes at least one X-ray source and at least one X-ray detector and is mounted on the outlet aperture of the irradiation unit.

SUMMARY AND DESCRIPTION

The present embodiments may obviate one or more of the drawbacks inherent in the related art. For example, in one embodiment, imaging, without restricting the rotation of an irradiation unit, is enabled in a particle therapy system.

In one embodiment, a particle therapy system includes a rotatable gantry with an irradiation unit. The irradiation unit projects into an irradiation room delimited by a wall. The imaging unit is arranged on a C-arm. The C-arm may be moved between a retracted parking position and an extended diagnostic position for imaging purposes.

A particle therapy system may include an irradiation unit and an imaging unit. Failure-free operation of the irradiation unit is enabled by movements of the two units being decoupled from one another. The imaging unit may be moved between a retracted parking position and an extended diagnostic position. The imaging unit includes a C-arm. At the two ends of the C-arm are arranged an X-ray source and an X-ray detector. The X-ray source and X-ray detector may be adjusted relative to a patient to be examined by the C-arm. DE 100 47 364 A1 discloses a C-arm. The irradiation unit of the gantry and the C-arm represent two separate units of the particle therapy system, which are controlled separately from each other for optimum positioning. The C-arm may be used for imaging from a number of positions without the irradiation unit, which is difficult to reposition, having to be moved. The C-arm may be arranged in a rear portion of the irradiation room at a distance from an exit window of the irradiation unit, such that the C-arm in its parking position crosses the line of motion of the irradiation unit only as little as possible or does not cross the line of motion of the irradiation unit at all.

For imaging in the irradiation room, the C-arm is moved to the diagnostic position. During the movement to the diagnostic position, the position of the patient couch (support) and the irradiation unit are taken into account, in order to avoid a possible collision. During the positional adjustment of the C-arm and the recording of images using the imaging unit, the irradiation unit remains stationary. Only after checks on the position of the patient by the imaging unit have been completed and the C-arm has returned to its parking position, which is outside the trajectory of the irradiation unit, is the irradiation unit moved to a position from which the radiation therapy is performed. Alternatively, it is also possible for the C-arm to intersect the trajectory of the irradiation unit, both in its diagnostic and its parking position. In this case, more complex control procedures are required, so that in the event of an impending collision between the irradiation unit and the C-arm this is diverted in a timely manner.

In one embodiment, the C-arm is mounted on the wall of the irradiation room in such a way that it also rotates in conjunction with rotation of the gantry. The C-arm may be connected to the gantry in such a way that in a rest position, in which it does not intersect the trajectory of the irradiation unit, it rotates along with the gantry. Control of the C-arm may be significantly facilitated, since in the retracted parking position it need not be readjusted relative to the further gantry components.

In order to minimize the space taken up in the irradiation room, the C-arm may abut the rear wall of the irradiation room in the retracted position with one side of the arc. The C-arm may be positioned such that C-arm extensively abuts the rear wall with one side of the arc.

In another embodiment, a recess for the C-arm is provided on the rear wall. The recess may be embodied in such a way that when the C-arm is in a parking position, the C-arm lies completely out of reach of the patient couch (support) and/or the outlet aperture.

The recess may be circular. The recess may be rotationally symmetrical and optimally matched to the form of the C-arm. The C-arm may rotate around the C-arm's mid point, even if the C-arm is located in the recess, so that it takes up an optimal parking position.

In one embodiment, a holding device for the C-arm may be mounted on the rear wall. The C-arm may be moved relative to the rear wall with the aid of the holding device. The holding device may be mounted in such a way that the holding device can be moved into the irradiation room and back to the rear wall, whereby the C-arm is brought into its extended diagnostic position or into its retracted parking position.

The functionality of the holding device may be extended by the C-arm being mounted on the holding device in such a way that it can be rotated through at least 180° (e.g., through 200°) around its mid point. The holding device may be used to record images of the patient from at least the most relevant angles for imaging purposes. In order to obtain images from further angles, the rotation of the C-arm may be combined with the positioning of the patient couch (support), which has a number of levels of freedom of movement.

To reduce the risk of a collision with the outlet aperture of the irradiation unit, the C-arm is attached in a pivotable manner. The C-arm, in the extended position, may be arranged inclined to the vertical. Due to the inclined position of the C-arm, the imaging unit includes a further degree of freedom in its positioning for imaging purposes. As a result of the inclination, the movement levels of the C-arm and the irradiation unit differ so much from each other that a collision is avoided.

An attachment point of the C-arm and the irradiation unit may be arranged diametrically opposite each other. The C-arm and the irradiation unit may be in two opposite areas of the irradiation room.

BRIEF DESCRIPTION OF THE DRAWINGS

An exemplary embodiment of the invention is described in greater detail on the basis of a drawing, where.

DETAILED DESCRIPTION

In the figures, parts operating in a similar manner are identified by identical reference numbers.

Figure 1:
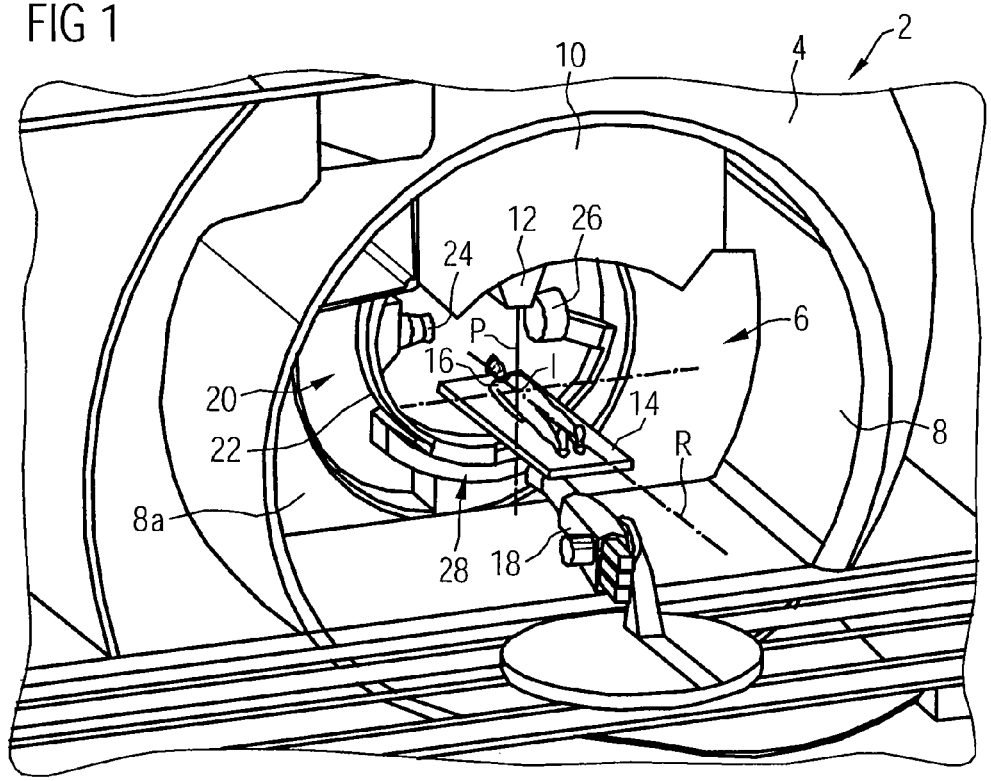
FIG. 1 shows one embodiment of a gantry of a particle therapy system with a C-arm in a parking position.

FIG. 1 shows a particle therapy system 2. The particle therapy system 2 includes a rotatable gantry 4, which can be rotated through 360° around an axis of rotation R. The gantry 4 may include a cylindrically embodied irradiation room 6, which is delimited by a wall 8. The gantry 4 includes an irradiation unit 10, from which an outlet aperture 12 projects into the irradiation room 6. A particle beam P, for example, an ion or proton beam, for the treatment of a patient 16 lying on a patient couch (support) 14, is guided in an irradiation channel of the gantry 4. The particle beam P enters the irradiation room 6 via the outlet aperture 12.

The patient couch 14 is positioned in the irradiation room 6 by a patient handling system, such as a controlled robot 18. The patient couch 14 is positioned in such a way that the tissue of the patient 16 to be irradiated lies in an isocenter I of the gantry. The robot 18 is, for example, a multiaxis industrial robot with a multipart mechanism, and is attached outside the irradiation room 6. The robot 18 may be used to move the patient couch 14 in a translatory manner in the horizontal and vertical direction. The robot 18 and the patient couch 14 may be rotated around different axes. The movement of the patient couch 14 is distinguished by three degrees of translatory freedom and three degrees of rotational freedom. As a result of the translatory and rotational movements of the patient couch 14, the tissue of the patient 16 to be irradiated is positioned in the isocenter I. A suitable position and distance of the patient 16 is set relative to the outlet aperture 12.

Figure 2:
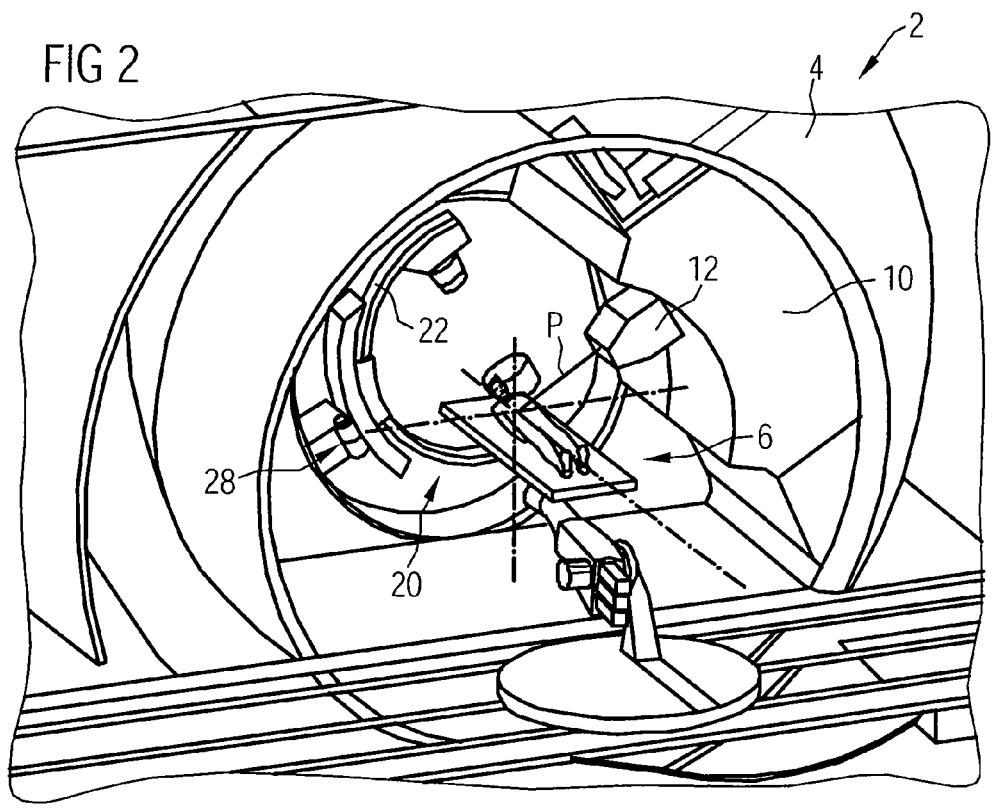
FIG. 2 shows the gantry according to FIG. 1 after rotation through about 60°.

Part of the wall 8 of the irradiation room 6 may be formed by a rear wall 8a, which delimits the irradiation room 6 to the rear, and rotates with the gantry 4 around the axis of rotation R. A recess 20 may be disposed on the rear wall 8a of the irradiation room 6. A C-arm 22, as shown in FIG. 1, may be moved into the recess 20 in a parking position. An imaging unit is arranged on the C-arm 22, including an X-ray source 24 and an X-ray detector 26. The C-arm 22 is attached to the rear wall 8a by a holding device 28. The holding device 28 is mounted on the rear wall 8a in such a way that so that in the case of a rotation of the gantry 4, the holding device 28 carrying the C-arm 22 also rotates, together with the rear wall 8a, as shown in FIG. 2.

The form of the recess 20 is matched to the form of the C-arm 22. The recess 20 may be circular. In a retracted position, the C-arm lies against the rear wall 8a in the area of the recess 20, so that it lies outside the reach of the patient couch 14 or the irradiation unit 10 when they are moved. The C-arm 22 may be arranged in the parking position opposite the irradiation unit 10, so that the C-arm 22 and the irradiation unit 10 are located in opposite areas of the irradiation room 6.

Figure 3:
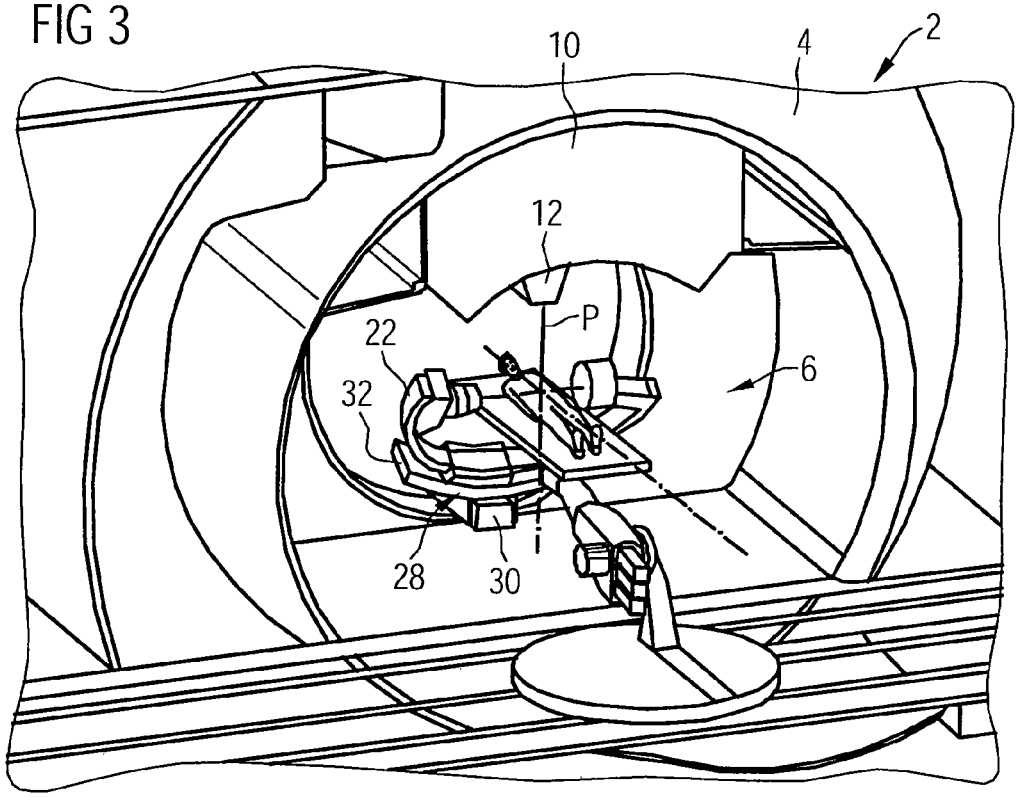
FIG. 3 shows the gantry according to FIG. 1, where the C-arm is in a diagnostic position.
Figure 4:
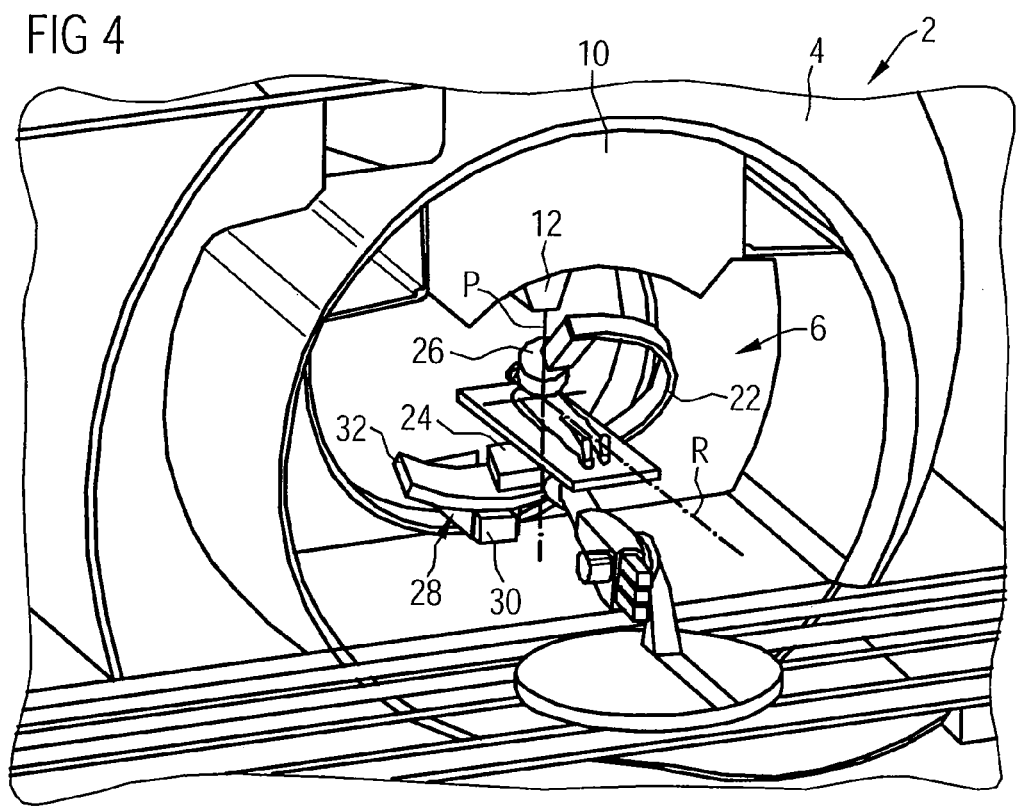
FIG. 4 shows the arrangement according to FIG. 3, where the C-arm is additionally turned through 90° relative to its mid point.

As shown in FIGS. 3 and 4, for imaging purposes for position verification of the patient 16, the C-arm 22 is moved out of the parking position in the recess 20 into a diagnostic position in the irradiation room 6. A holding arm 30 of the holding device 28 is extended from the rear wall 8a. The holding arm 30 may, for example, be telescopic. Alternatively, the holding arm 30 may be connected to a slide-in mechanism arranged behind the rear wall 8a, enabling the holding arm 30 to be conveyed deeper into the irradiation room 6 or back to the rear wall 8a.

The holding device 28 may include a curved element 32. The curved element 32 may be arranged on the holding arm 30 in a pivotable manner. The pivoting function of the curved element 32 allows the C-arm 22, in its extended diagnostic position, to be inclined to the vertical, so that the C-arm 22 extends in the vertical direction to a lesser degree than if it stood vertically, in order, through its inclined position, to reduce the risk of a collision with the outlet aperture 12.

As shown in FIG. 4, the C-arm may be conveyed along the curved element 32 of the holding device 28, so that the C-arm 22 can rotate about its mid point. In one exemplary embodiment, the C-arm 22 can be rotated by ±100° around its mid point, starting from its position, as shown in FIG. 3. In the arrangement shown in FIG. 4, the C-arm 22 is rotated through 90°, so that a line joining the X-ray source 24 and the X-ray detector 26 lies at the level at which the axis of rotation R and the vertically oriented particle beam P intersect.

Various embodiments described herein can be used alone or in combination with one another. The forgoing detailed description has described only a few of the many possible implementations of the present invention. For this reason, this detailed description is intended by way of illustration, and not by way of limitation. It is only the following claims, including all equivalents that are intended to define the scope of this invention.

The invention claimed is:

1. A particle therapy system comprising:
a rotatable gantry with an irradiation unit, which projects into an irradiation room delimited by a wall, and
an imaging unit on a C-arm,
wherein the C-arm is operable to be moved between a retracted parking position and an extended diagnostic position for imaging purposes.

2. The particle therapy system as claimed in claim 1, wherein the C-arm is mounted on the wall of the irradiation room, such that C-arm is operable to rotate along with a rotation of the gantry.

3. The particle therapy system as claimed in claim 1, wherein the C-arm, in its retracted position, lies against a rear wall of the irradiation room.

4. The particle therapy system as claimed in claim 2, wherein the rear wall includes a recess for the C-arm.

5. The particle therapy system as claimed in claim 4, wherein the recess is circular.

6. The particle therapy system as claimed in claim 3, wherein the rear wall includes a holding device for the C-arm, the holding device being operable to be moved relative to the rear wall.

7. The particle therapy system as claimed in claim 6, wherein the C-arm is mounted on the holding device such that the C-arm is operable to be rotated by at least 180° around its midpoint.

8. The particle therapy system as claimed in claim 1, wherein the C-arm is fixed in a pivotable manner and in its extended position is arranged inclined to the vertical.

9. The particle therapy system as claimed in claim 1, wherein the C-arm and the irradiation unit are arranged opposite to each other.

10. The particle therapy system as claimed in claim 7, wherein the C-arm is mounted on the holding device in such a way that the C-arm is operable to be rotated by 200° around its mid point.

11. The particle therapy system as claimed in claim 2, wherein the C-arm, in its retracted position, lies against a rear wall of the irradiation room.

12. The particle therapy system as claimed in claim 11, wherein the rear wall includes a recess for the C-arm.

13. The particle therapy system as claimed in claim 12, wherein the recess is circular.

14. The particle therapy system as claimed in claim 13, wherein the rear wall includes a holding device for the C-arm, the holding device being operable to be moved relative to the rear wall.

15. The particle therapy system as claimed in claim 14, wherein the C-arm is mounted on the holding device such that the C-arm is operable to be rotated by at least 180° around its midpoint.

* * * * *